United States Patent
Zardi et al.

(10) Patent No.: US 8,129,565 B2
(45) Date of Patent: Mar. 6, 2012

(54) HIGH-PRESSURE LOOP IN A PROCESS FOR SYNTHESIS OF UREA

(75) Inventors: Federico Zardi, Breganzona (CH); Andrea Scotto, Breganzona (CH)

(73) Assignee: Urea Casale S.A. (CH)

( * ) Notice: Subject to any disclaimer, the term of this patent is extended or adjusted under 35 U.S.C. 154(b) by 0 days.

(21) Appl. No.: 13/140,286

(22) PCT Filed: Nov. 17, 2009

(86) PCT No.: PCT/EP2009/065294
§ 371 (c)(1),
(2), (4) Date: Sep. 1, 2011

(87) PCT Pub. No.: WO2010/069691
PCT Pub. Date: Jun. 24, 2010

(65) Prior Publication Data
US 2011/0306791 A1     Dec. 15, 2011

(30) Foreign Application Priority Data
Dec. 17, 2008  (EP) .................................... 08021875

(51) Int. Cl.
*C07C 273/04* (2006.01)
(52) U.S. Cl. ................. 564/67; 564/70; 564/71; 564/72

(58) Field of Classification Search .................... 564/67, 564/70, 71, 72
See application file for complete search history.

(56) References Cited

U.S. PATENT DOCUMENTS

| 4,613,696 A | 9/1986 | Zardi |
| 5,849,952 A | 12/1998 | Carloni et al. |

FOREIGN PATENT DOCUMENTS

EP   0504966 A1   9/1992

OTHER PUBLICATIONS

International Preliminary Report on Patentability based on PCT/EP2009/065294.

*Primary Examiner* — Peter O Sullivan
(74) *Attorney, Agent, or Firm* — Akerman Senterfitt

(57) ABSTRACT

A process and a related plant layout for producing urea are disclosed, wherein the high-pressure loop (1) comprises a synthesis reactor (2), a thermal stripper (3), a condenser (4), and an adiabatic $CO_2$ stripper (10) disposed upstream said thermal stripper, separating a vapour phase (13) containing ammonia from the urea solution (9) discharged from the reactor, and recycling said vapour phase to the reactor. The adiabatic stripper (10) can be incorporated in a reactor (200) having a top reaction zone and a bottom adiabatic stripping zone. A revamping method for a conventional urea plant in accordance with the inventive process is also disclosed.

10 Claims, 4 Drawing Sheets

HIGH-PRESSURE LOOP IN A PROCESS FOR SYNTHESIS OF UREA

DESCRIPTION

1. Field of the invention

The present invention refers to a new process for production of urea. The invention provides an improvement of the high-pressure synthesis loop of conventional processes and is suitable for new plants as well as for the revamping of existing self-stripping and carbon-dioxide stripping urea plants.

2. Prior Art

The self-stripping or thermal-stripping process is a well known process for the synthesis of urea. It is often referred to as the Snamprogetti process, having been developed by Snamprogetti in the late 60s. A disclosure of the process and related plant can be found for example in GB 1542371. Many urea plants are using this process worldwide.

Basically, the self-stripping process provides reaction between ammonia $NH_3$ and carbon dioxide $CO_2$ in a high pressure reactor around 150-160 bar. The nitrogen to carbon ratio N/C in the reactor is usually around 3.2-3.4 molar.

An aqueous urea solution containing free unreacted ammonia and unconverted ammonium carbamate is discharged by the reactor. This urea solution is heated in a high-pressure stripper to decompose the carbamate and recover ammonia and $CO_2$. A vapour phase containing ammonia and $CO_2$ produced in the stripper is condensed in a high-pressure condenser and recycled to said reactor. The reactor, the stripper and the condenser form the so-called high-pressure section or high-pressure loop.

Usually the plant comprises also a recovery section with a medium-pressure (MP) and a low-pressure (LP) decomposition section to further dissociate the ammonium carbamate and recycle the carbamate together with ammonia to the reaction zone.

The stripper is usually a heat exchanger where the urea solution coming from the reactor is fed to a steam-heated tube bundle, without additional use of a stripping gas. Heat supplied by the steam results in the partial decomposition of the carbamate into carbon dioxide and ammonia which, together with part of the free ammonia, are recovered at the top of the stripper. In some cases, ammonia is used as a stripping agent.

The condenser is usually a shell-and-tube, horizontal kettle unit, where the gaseous phase is condensed on the tube side in the presence of the recycled carbamate solution recovered from the MP and LP sections and used as a condensation liquid. The condensation heat is used to produce steam.

The yield of conversion in the reactor is relatively low, generally around 60%. It is known that the conversion yield can be higher if the reactor is operated with higher ammonia excess; this however would discharge a surplus of ammonia to the stripper and the downstream medium and low-pressure sections, increasing the duty of these equipments, since the excess of ammonia has to be separated and condensed in the MP/LP section(s). For these reasons, the reactor is usually run at NC ratio less than 3.2-3.4.

Hence, there is the need to ameliorate the yield of conversion without the drawback of increasing the duty of the MP and LP sections. This need is felt for new plants as well as for the revamping of existing self-stripping urea plants, operating with the above process. In this specification, the term "revamping" indicates the modification of an existing plant, in order to improve its performance and obtain, for example, a larger production capacity and/or a better conversion yield, or else to reduce the energy consumption, reducing for example the steam furnished to the stripper.

Another well-known process is the $CO_2$-stripping process, where carbon dioxide is fed to the high-pressure stripper as a stripping medium. The $CO_2$-stripping process has some advantageous features, but has a limitation in the large size of the equipments, especially the stripper. This limitation is felt particularly in large plants, e.g. over 3.500 tons/day of urea.

SUMMARY OF THE INVENTION

The technical problem of the present invention is to overcome the above drawbacks of the prior-art processes for the synthesis of urea.

The invention discloses a process where ammonia and carbon dioxide are reacted in a high-pressure loop comprising at least a synthesis reactor, a thermal stripping section and a carbamate condensation section, the process being characterized in that:

a urea solution produced in said reactor is subjected to an adiabatic stripping process in an adiabatic stripping section, with carbon dioxide as a stripping medium, obtaining a liquid urea solution and a vapour phase containing ammonia and carbon dioxide;

said urea solution obtained in said adiabatic stripping process is further subject to thermal stripping in said thermal stripping section;

said vapour phase is recycled to the reaction zone in said synthesis reactor.

According to one aspect of the invention, the adiabatic stripping process is regulated so that the N/C ratio in the synthesis reactor is greater than the N/C ratio of the urea solution at the inlet of the thermal stripping section.

Preferably, the synthesis reactor is run at a N/C ratio between 4 and 6, and more preferably around 4.5, while the N/C ratio at the inlet of the thermal stripping section is maintained around 2 to 4, preferably 2.6.

The term of "thermal stripping section" is used in this specification with reference to a stripping section where the stripping process involves a heat input for example by steam heating, thus including a self-stripping unit with no addition of any stripping medium, or a CO2-stripping unit where dissociation of the solution of urea is also promoted by a carbon dioxide stream.

Hence, an aspect of the invention provides that some carbon dioxide is fed to said thermal stripping section, for use as a stripping medium. In a preferred embodiment, the total carbon dioxide feed is split into a first portion directed to the adiabatic stripping section; a second portion directed to the reactor, and a third portion directed to the thermal stripping section. Preferably 20% to 60% of the total carbon dioxide feed is sent to the adiabatic stripping section, and the remaining portion is split between the reactor and the stripping section. Said remaining portion is more preferably divided in substantially equal parts between the reactor and the stripping section.

The adiabatic stripping process is carried out substantially at the same pressure of the reactor. The adiabatic stripping section can be realized, according to different embodiments, with external unit(s) between the reactor and the existing stripping section, or with a stripping unit incorporated in the reactor itself. In this specification, for the sake of simplicity, reference is also made to a thermal or adiabatic "stripper", meaning the aforesaid stripping sections.

The inventive process is a substantial amelioration of the known techniques for producing urea, including the conventional self-stripping process and the $CO_2$-stripping process.

The invention provides a first loop for re-circulation of ammonia, comprising the reactor and the adiabatic stripper, and a second loop comprising the adiabatic stripper and the thermal stripper. Hence, the N/C ratio in the reactor is made independent, between certain limits, from the N/C ratio in the thermal stripper and the recovery section. This degree of freedom can be used to enhance the conversion yield without having the undesired counterpart of an ammonia surplus discharged to the stripper and MP/LP section.

Then, the reactor can be operated with some ammonia excess, keeping the N/C ratio in the thermal stripper and in the recovery section substantially unchanged. Depending on the circumstances, the conversion yield can reach 68-75% compared to the 60% about of a conventional self-stripping plant.

Another advantage is that the steam consumed by the thermal stripper is reduced, usually by 15-30%, thanks to the N/C ratio in the reactor. This reduced consumption is per se an advantage, and leaves a margin for increasing the capacity of the whole plant. Feeding a portion of the $CO_2$ to the thermal stripper has the further advantage that less ammonia need to be recovered in the downstream MP section. Recycled $NH_3$ and carbamate can be reduced by around 30%. In a new plant, this means that the medium-pressure section is simpler and less expensive than in the prior art, for a given urea capacity; in the revamping of an old plant, this means that some equipments of the MP section can be shut down or—on the other hand—the existing MP section offers a significant margin to increase the production rate.

Another advantage over the conventional self-stripping process is that the N/C ratio in the condenser can be reduced, allowing a higher condensation temperature. The N/C ratio of the solution at the outlet of the condenser is preferably 2 to 3.5, and more preferably 2.5, i.e. significantly lower than the values of 3.5-4 which are used in the prior-art. This means a higher delta-T (difference of temperature) in the condenser and thus a more effective condensation. Another related advantage is that more urea is formed in the condenser, due to the higher temperature.

The HC ratio (between $H_2O$ and $CO_2$) is also lowered, with a positive effect of right-shifting the equilibrium of the reaction, as water is a product. In a self-stripping plant, for example, said HC ratio passes from the typical value of 0.9 to a lower value of 0.6-0.7.

A plant for the production of urea adapted to operate according to the above process comprises a high-pressure loop with at least a synthesis reactor receiving an ammonia feed and a carbon dioxide feed, a thermal stripping section comprising at least one stripper, and a condensation section comprising at least one carbamate condenser, and is characterized by:
  at least a further stripping section, operating as adiabatic carbon dioxide stripping section and provided between the reactor and the thermal stripping section;
  means for feeding the urea solution produced in said reactor to said adiabatic stripping section, and means feeding a urea solution recovered from said adiabatic stripping section to the downstream thermal stripping section;
  means for recycling a gaseous phase recovered in said adiabatic stripping section, and containing carbon dioxide and ammonia, to the reaction zone in said synthesis reactor.

As above, the reference to "thermal stripping section" means a stripping section comprising at least one heated (e.g. steam-heated) stripper, which may operate according to the self-stripping or $CO_2$-stripping process.

In a further embodiment, the stripping section is incorporated in the reactor, said reactor comprising an upper reaction zone and a lower adiabatic-stripping zone. Said lower stripping zone receives the liquid urea solution coming from the upper reaction zone. The reactor comprises appropriate means for feeding a carbon dioxide flow and a flow of ammonia plus recycled carbamate to the upper reaction zone, as well as means for feeding a further $CO_2$ stream to said adiabatic-stripping zone, for use as a stripping medium.

In a preferred embodiment, the reactor comprises a plurality of gas-liquid contacting devices in said lower adiabatic-stripping zone; a liquid distributor receiving urea and carbamate solution from the upper reaction zone and distributing said solution over said gas-liquid contacting devices; a bottom gas distributor providing the $CO_2$ feed in the adiabatic-stripping zone; a liquid seal realized preferably with a chimney, separating the upper reaction zone from the lower adiabatic-stripping zone. Said liquid seal allows to recycle a vapour phase containing ammonia and carbon dioxide, released in the lower stripping zone, to the upper reaction zone of the reactor.

A further aspect of the invention is a method for revamping an existing urea plant, in order to carry out the above process. The method is applicable to native self-stripping or $CO_2$-stripping urea plants, comprising a high-pressure synthesis loop with at least a synthesis reactor receiving an ammonia feed and a carbon dioxide feed, a stripping section comprising at least one stripper, and a condensation section comprising at least one carbamate condenser, the method being characterized by:
  providing at least a further adiabatic carbon dioxide stripping section;
  providing appropriate means for feeding the urea solution produced in said reactor to said adiabatic stripping section, and feeding a urea solution recovered from said adiabatic stripping section to the downstream stripping section;
  providing further means for recycling a gaseous phase containing carbon dioxide and ammonia recovered in said adiabatic stripping section to the reaction zone in said synthesis reactor.

The further adiabatic stripping section is added downstream the reactor and upstream the location, in the plant layout, of the existing stripping section.

In a first embodiment of the revamping method, the further adiabatic stripping section is realized by adding at least one stripping unit to the original layout. In a second embodiment of the method, the further adiabatic stripping section is realized by modifying the existing reactor, or replacing it with a new one, so that the adiabatic stripping section is integrated in the synthesis reactor.

The modified or new reactor comprises an upper reaction zone and a lower adiabatic-stripping zone, as disclosed above. Appropriate means are provided for feeding the upper reaction zone with a flow of ammonia plus recycled carbamate, and a carbon dioxide flow; and for feeding a further $CO_2$ to the newly added adiabatic-stripping zone. A conventional reactor can be modified by: adding a chimney with a liquid seal, separating an upper reaction zone from a lower adiabatic-stripping zone; installing a plurality of gas/liquid contacting devices in said lower adiabatic-stripping zone; providing a liquid distributor receiving urea and carbamate solution from the upper reaction zone and distributing said solution over the gas/liquid contacting devices; installing a gas distributor preferably at the bottom of the reactor, providing the $CO_2$ feed in the lower adiabatic-stripping zone.

The existing carbon dioxide feed, is preferably modified so that, in operation, a first portion of the total available $CO_2$ is directed to said adiabatic stripping section; a second portion is directed to the reactor and a third portion is directed to the thermal stripping section for use as a stripping agent.

Advantageously, the revamped plant is run with a N/C ratio in the reactor between 4 and 6 and preferably around 4.5, i.e. with a significant excess of ammonia in comparison with a standard self-stripping process, achieving the advantage of a better conversion. This is possible thanks to the loop between the reactor and the new adiabatic stripper, recycling the ammonia surplus to the same reactor without affecting the downstream equipments and the recovery section.

An advantage of the revamping of self-stripping plants according to the invention is also the following. The stripper of a conventional self-stripping plant is limited by the so-called flooding, due to excess of gas in the tubes. Hence no or very little $CO_2$ can be fed additionally to the stripper, as a stripping medium. Thanks to the better conversion in the reactor, achieved by the invention, there is less gas generated in the stripper, and the existing stripper can tolerate more additional $CO_2$ as a stripping medium and, as a further consequence, less $NH_3$ is released to the recovery section downstream, with the above said advantages of a simpler and less expensive recovery section.

An advantage of the invention over the conventional $CO_2$-stripping process is the reduced size of the equipments relative to the capacity, and then the easier achievement of huge production rates as for example 4.000-5.000 tons/day of urea.

Further characteristics and advantages of the invention shall become clearer from the following description of some example embodiments, with reference to the attached drawings.

DETAILED DESCRIPTION OF PREFERRED EMBODIMENTS

Figure 1:
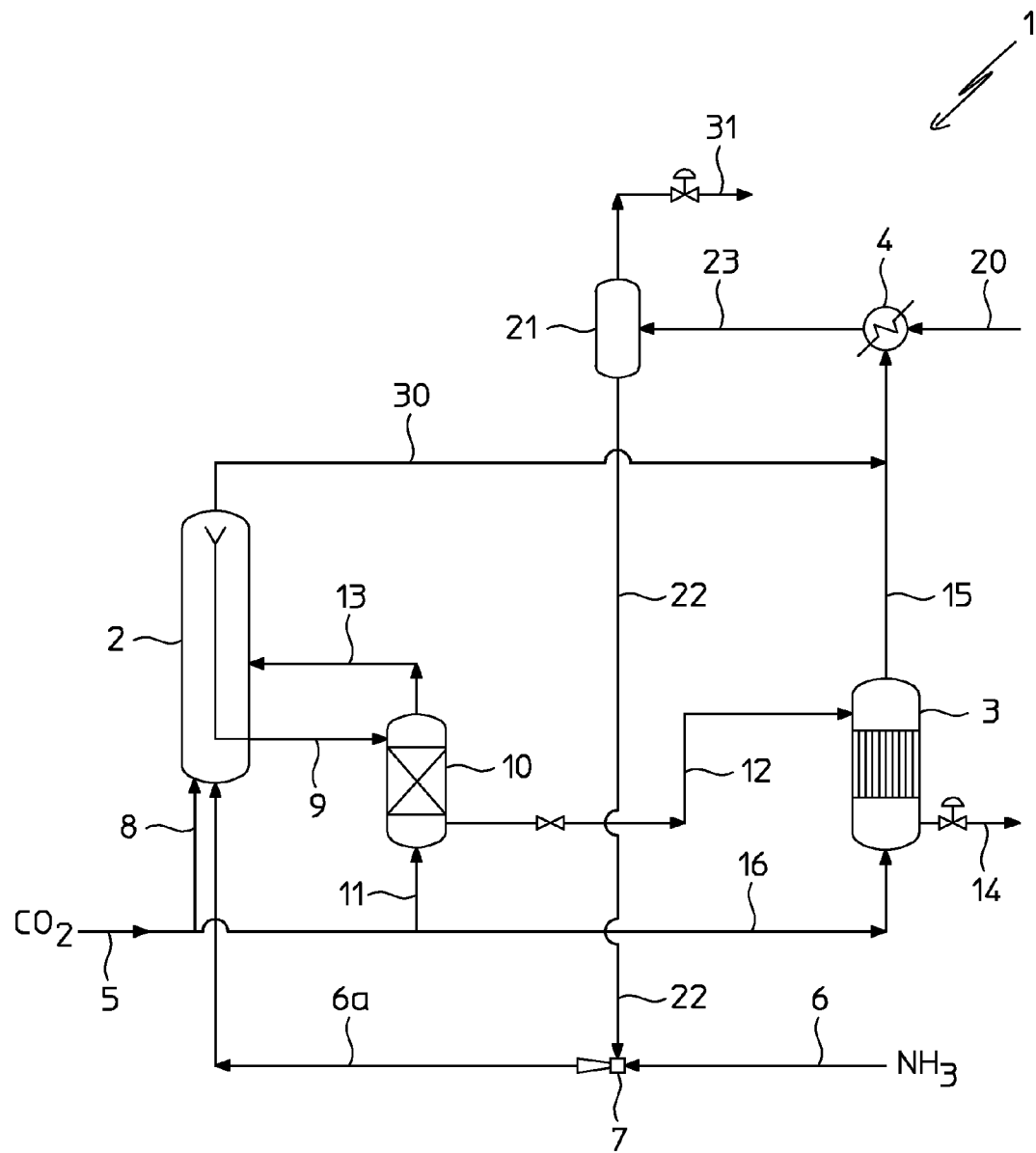
FIG. 1 is a simplified scheme of a urea plant according to a first embodiment of the invention.

Referring to FIG. 1, the high-pressure synthesis loop 1 of a plant for the production of urea basically comprises a reactor 2 containing a reaction zone, a steam-heated thermal stripper 3 and a condenser 4.

Carbon dioxide is fed via a line 5 and ammonia is fed via a line 6 and through an ejector 7. The carbon dioxide enters the reactor 2 via a line 8, and is reacted with the ammonia forming an acqueous urea solution 9 containing urea, ammonium carbamate and ammonia.

Said solution 9 is sent to an adiabatic stripper 10, also receiving a feed 11 of carbon dioxide. The adiabatic stripper 10 is located between the reactor 2 and the steam-heated stripper 3, i.e. upstream said stripper 3.

The output of the adiabatic stripper 10 is a urea solution 12 containing urea and ammonium carbamate, with a lower ammonia content than the inlet solution 9, and a gaseous phase 13 containing ammonia and $CO_2$. Said urea solution 12 is sent to the downstream thermal stripper 3, while the gaseous phase 13 is recycled to the reaction zone of the reactor 2.

The stripped urea solution 14 released from the stripper 3 is sent to medium and low-pressure recovery sections, not shown, while the gaseous phase 15 obtained in the same stripper 3 is condensed in the condenser 4 and recycled back to the reactor 2. In particular, the condenser 4 receives the gaseous phase 15 together with non-condensable gases 30 purged from the reactor 2, and a stream of recycled carbamate 20 coming from the recovery section; the condensate 23 is sent to a separator 21 and then to the ejector 7, via a line 22, entering the reactor 2 in the line 6a, together with the fresh ammonia feed 6. Non-condensable gases are discharged from separator 21 at the flow line 31. These details are known in the art, and thus they are not described in greater detail.

It should be noted, in particular, that the adiabatic stripper 10 provides an intermediate loop allowing to recirculate the ammonia contained in the urea solution 9 to the reactor itself. Hence, the N/C ratio (mol $NH_3$/mol $CO_2$) inside reactor 2 can be greater than the N/C ratio inside the downstream stripper 3. In a preferred embodiment of the inventive process, the reactor 2 operates at a N/C ratio around 4.5, while the N/C ratio in the stripper 3 is around 2.6.

A part 16 of the available $CO_2$ feed 5 is directed to the steam-heated stripper 3, to further promote the dissociation of the carbamate contained in the solution 12. Preferably, the $CO_2$ feed 5 is split around 50% to the adiabatic stripper (line 11), 30% to the reactor 2 (line 8), and 20% to the stripper 3 (line 16).

In a variant of the invention, the $CO_2$ stream 16 can be fed at the top of the stripper 3, instead of bottom as shown. Feeding the stream 16 to the top of the stripper 3 is appropriate especially when the plant 1 is obtained by revamping an existing plant with a relatively small stripper 3, and replacement with a larger stripper is deemed not convenient.

The layout of the loop 1 can be a part of a new plant or may result from revamping of an existing urea plant. A revamping of a self-stripping plant according to the invention is now described in greater detail.

The high-pressure loop of an existing plant comprises for example the reactor 2, the steam-heated stripper 3 and the condenser 4. The urea solution 9 is originally sent directly to the stripper 3 and the $CO_2$ feed, as usual, is directed to the reactor only. The stripper 3 is substantially a steam-heated tube-bundle exchanger; the condenser 4 is a horizontal shell-and-tube kettle unit where condensation is effected on the tube side, and the condensation heat is used to produce steam.

The intervention for revamping said plant involves at least the provision of the new unit 10 and of the related flow lines and auxiliary equipments such as valves, pumps, etc. in order to carry out the inventive process.

Referring again to the layout of FIG. 1, the revamping can be carried out by adding the adiabatic stripper 10 and the related $CO_2$ feed 11, upstream the existing unit 3; providing the flow line feeding the urea solution 9, discharged from the reactor 2, to said new stripper 10; providing the flow line feeding the urea solution 12 from the new stripper 10 to the original thermal stripper 3; providing the flow line feeding the gaseous phase 13, recovered at top of the new stripper 10, to the reactor 2. The original stripper 3 and/or the original condenser 4 may also be revamped or replaced, in equivalent embodiments of the invention and in accordance with the specific needs.

Preferably the $CO_2$ feeding line is modified so as to provide the $CO_2$ feeds 8, 11 and 16 to the reactor 2, the adiabatic stripper 10 and the thermal stripper 3, respectively, so using the carbon dioxide as a stripping medium.

In operation, the new unit 10 allows to maintain an excess of ammonia in the reactor 2, without discharging the surplus of ammonia to the stripper 3 and to the flow 14 directed to the downstream recovery section. The surplus ammonia, in fact, is removed from the stream 9 in the unit 10, and recycled to the same reactor 2 via the gaseous flow 13. This means that the conversion yield can be increased without affecting the duty of the recovery section.

Figure 2:
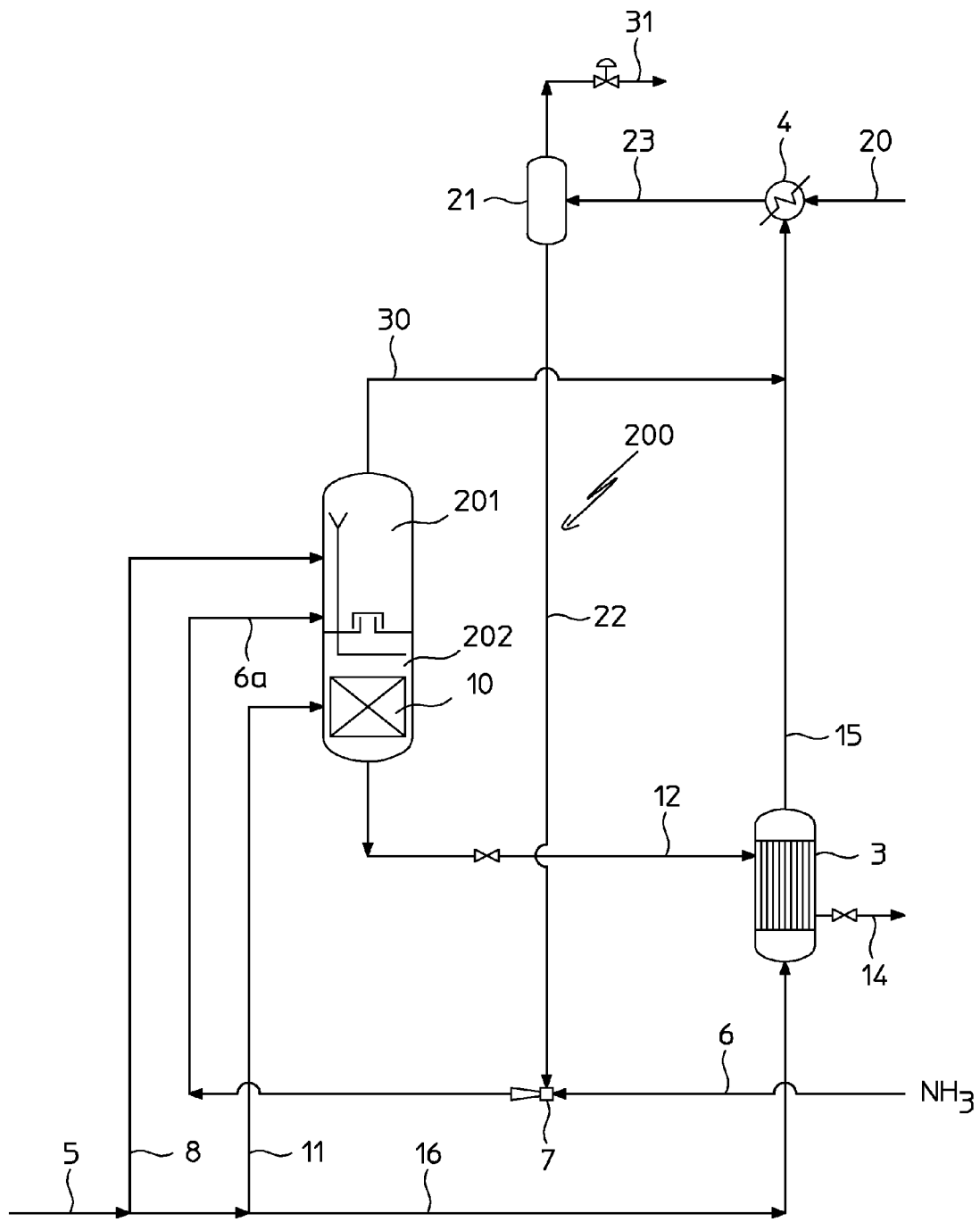
FIG. 2 is a simplified scheme of a urea plant according to a second embodiment of the invention.

FIG. 2 refers to an embodiment of the invention where the adiabatic stripper 10 is integrated in a stripping zone 202 of the reactor. A reactor 200 comprises substantially an upper reaction zone 201 and an adiabatic-stripping zone 202 where the liquid urea solution coming from the upper zone 201 is passed over a series of trays or packing, and adiabatic stripping takes place with the aid of the further $CO_2$ feed 11. The reaction zone 201 is fed with the flow 6a of $NH_3$ plus carbamate, delivered by the ejector 7, and with the carbon dioxide flow 8. Preferably the adiabatic-stripping zone 202 is 10% to 20% of the available volume of reactor 200.

The reaction zone 201 and the adiabatic-stripping zone 202 are separated by a liquid seal, allowing the passage of gas from the lower zone 202 to the upper zone 201. The urea solution is taken at the bottom of the lower adiabatic-stripping zone 202 and sent to the thermal stripper 3. It should be noted that the flow lines 9 and 13 are not shown in FIG. 2 as the unit 10 is actually incorporated in the reactor 200. Arrangement of the other items, such as the condenser 4 and separator 21, is equivalent to FIG. 1.

Figure 3:
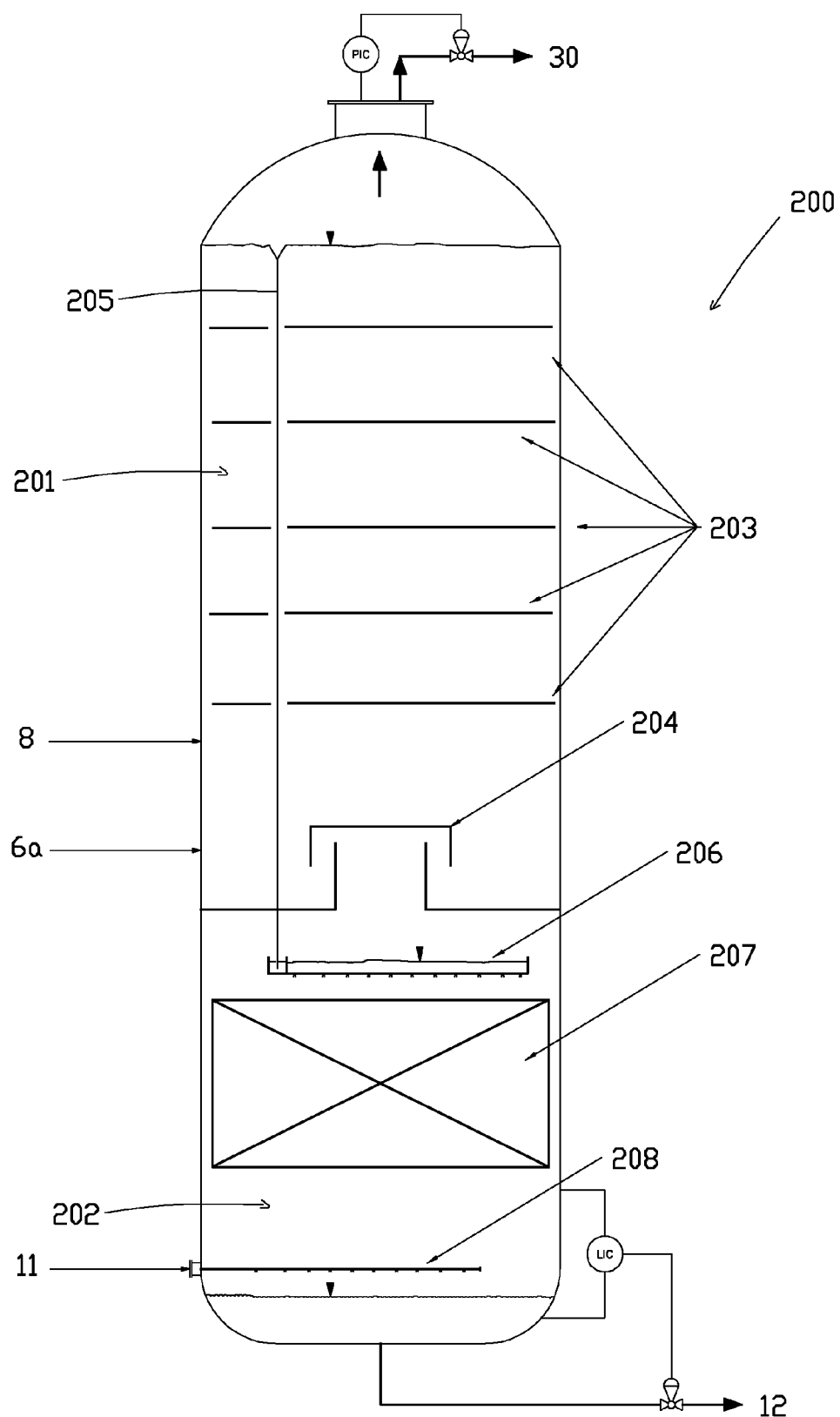
FIG. 3 is a sketch of the urea reactor of the plant of FIG. 2.

Details of a preferred embodiment of the reactor 200 are shown in FIG. 3. The upper reaction zone 201 comprises a series of trays 203, and is separated from the lower zone 202 by a chimney 204 with a liquid seal. The urea solution is produced in the zone 201, receiving the $NH_3$/carbamate feed 6a and the $CO_2$ feed 8, and is conveyed by a duct 205 on a liquid distributor 206, and then over a series of gas/liquid contacting devices which in this example are represented by trays 207, forming the adiabatic stripper 10 in the lower zone 202. Further carbon dioxide is supplied by a gas distributor 208 mounted at the bottom of the reactor and connected to the $CO_2$ input 11.

In operation, the liquid solution produced by the reaction in the upper zone 201 flows down through the duct 205 and distributor 206, over the trays 207, where it is stripped by the $CO_2$ feed 11. Said duct 205 and distributor 206 have the function of the flow line 9 in FIG. 1, while the chimney 204 has substantially the same function of the line 13 in the same FIG. 1, recycling the vapors produced in the adiabatic stripping zone 202 to the reaction zone 201. The solution is taken at line 12, equipped with a liquid level control, and sent to the thermal stripper. Non-condensable gases are discharged at line 30.

A conventional reactor can be revamped to the configuration of FIG. 3, removing some of the existing trays 203 so as to provide sufficient room at the bottom of the reactor for the trays 207 of the new stripping zone, and providing the gas distributor 208, liquid distributor 206 and chimney 204 for the liquid seal. The trays 203 and 207 can be removed and introduced via the manhole of the reactor, thus not requiring a substantial intervention on the shell. Weldings and modification of the input/outputs of the shell of the reactor are advantageously limited.

Figure 4:
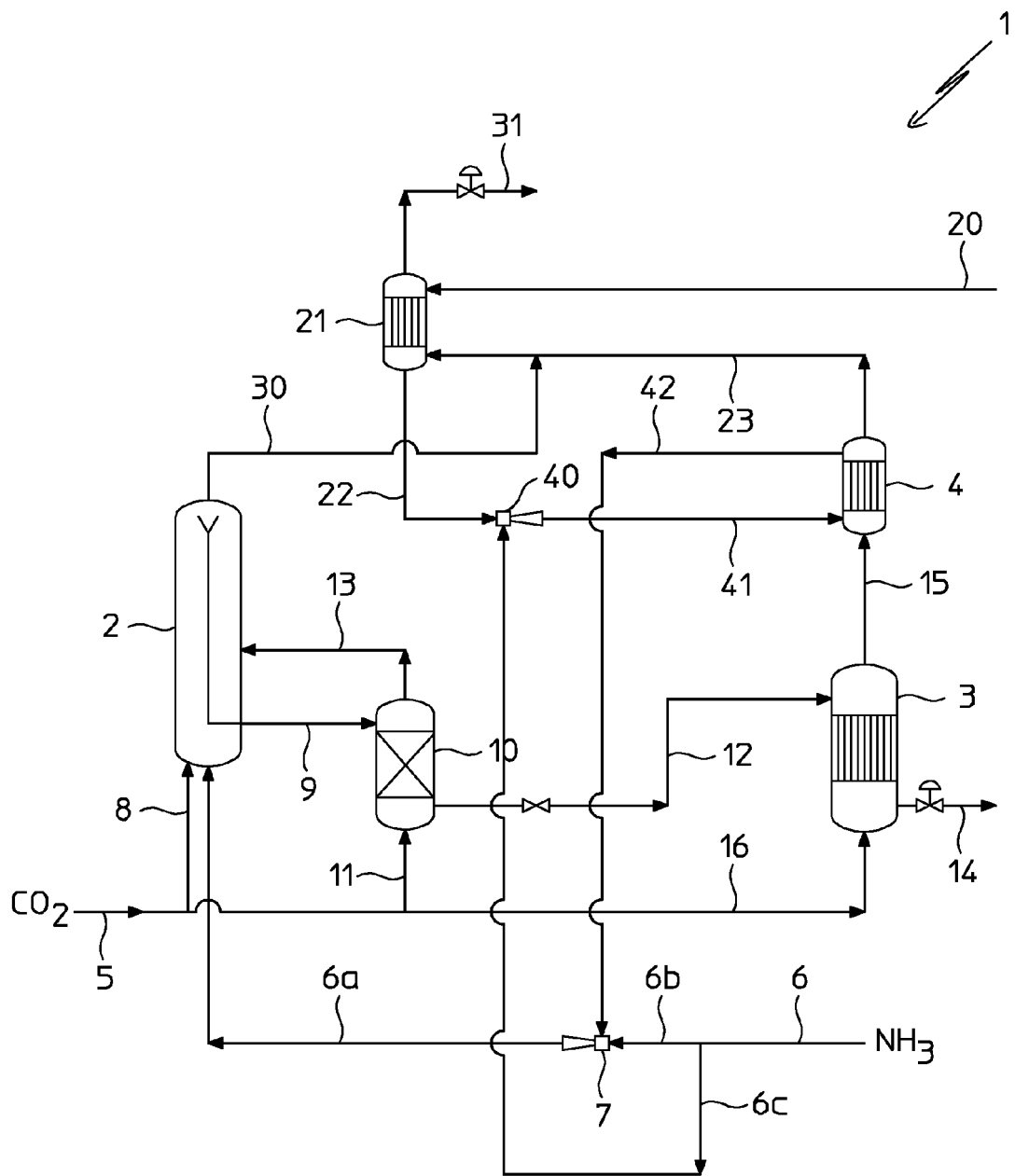
FIG. 4 is a layout of a urea plant according to a further embodiment of the invention.

FIG. 4 shows a further layout where items equivalent to those of FIG. 1 are indicated with the same numerals. The condenser 4 in this example is a vertical shell-and-tube unit, and the item 21 is a scrubber.

The $NH_3$ feed 6 is split into a first portion 6b directed to the ejector 7, and a second portion 6c is directed to a second ejector 40. The first ejector 7 receives the liquid stream 42 condensed in the condenser 4, while the second ejector 40 receives the liquid stream 22 from a scrubber 21. The output stream 41 of said ejector 40 is sent to the condenser 4 together with the gaseous phase 15 from the stripper 3. The residual gaseous phase 23 at the outlet of the condenser 4 is merged with the gaseous phase 30 from the reactor 2, and sent to the scrubber 21.

The $CO_2$ feed 5, also in this layout, is preferably divided into portions 8, 11 and 16 for the reactor, the adiabatic stripper 10 and the stripper 3.

The layout of FIG. 4 is preferably adopted for the revamping of a conventional $CO_2$-stripping plant. For example, a $CO_2$ stripping plant with a high-pressure loop comprising the main items of reactor 2, stripper 3, condenser 4 and scrubber 21, can be revamped by adding the adiabatic stripper 10 and related flow lines 9, 11, 12 and 13. Alternatively, the plant can be revamped by the provision of a modified reactor with integrated adiabatic stripping section 202 as in FIG. 3.

The invention claimed is:

1. A process for producing urea, where ammonia and carbon dioxide are reacted in a high-pressure loop comprising at least a synthesis reactor, a thermal stripping section and a carbamate condensation section, the process comprising the steps of:
   subjecting a urea solution produced by reacting the ammonia and carbon dioxide to an adiabatic stripping process in an adiabatic stripping section, with a carbon dioxide feed as a stripping medium, obtaining a liquid urea solution and a vapour phase containing ammonia and carbon dioxide,
   further subjecting the urea solution obtained in said adiabatic stripping process to thermal stripping in said thermal stripping section, and
   recycling said vapour phase to the reaction zone of said synthesis reactor,
   said thermal stripping section including a self-stripping unit with no addition of any stripping medium or a $CO_2$-stripping unit in which carbon dioxide is fed for use as a stripping medium, and a carbon dioxide feed is split into:
   a first portion sent to the adiabatic stripping section;
   a second portion sent to the reactor and
   a third portion sent to the thermal stripping section,
   said first portion of the carbon dioxide feed being 20 to 60% of the total feed.

2. The process according to claim 1, wherein said adiabatic stripping process is regulated so that the N/C ratio in the synthesis reactor is greater than N/C ratio at the inlet of the thermal stripping section.

3. The process according to claim 2, wherein the synthesis reactor is run with the N/C ratio between 4 and 6, while the N/C ratio of the urea solution at the inlet of the thermal stripping section is between 2 and 4.

4. The process according to claim 1, wherein the N/C ratio of the urea solution at the outlet of said condensation section is in the range 2 to 3.5.

5. The process according to claim 1, wherein said adiabatic stripping process is carried out substantially at the same pressure of the reactor of the high-pressure loop.

6. The plant for the production of urea adapted to operate according to the process of claim 1, the plant comprising:
   a high-pressure loop with at least a synthesis reactor receiving an ammonia feed and a carbon dioxide feed;
   a thermal stripping section comprising at least one stripper;
   a condensation section comprising at least one carbamate condenser,
   at least a further stripping section, operating as adiabatic carbon dioxide stripping section and provided between the reactor and the thermal stripping section;
   means feeding the urea solution produced in said reactor to said adiabatic stripping section, and means feeding a urea solution recovered from said adiabatic stripping section to the downstream thermal stripping section;

means recycling a gaseous phase recovered in said adiabatic stripping section, and containing carbon dioxide and ammonia, to the reaction zone in said synthesis reactor, wherein said further stripping section is incorporated in the reactor, said reactor comprising an upper reaction zone and a lower adiabatic-stripping zone receiving the liquid urea solution coming from the upper reaction zone, and said reactor further comprising appropriate means for:

feeding a carbon dioxide flow and a flow of ammonia plus recycled carbamate to the upper reaction zone; and feeding a further $CO_2$ stream to said adiabatic-stripping zone, for use as a stripping medium.

7. The plant according to claim 6, said reactor comprising:
a plurality of gas-liquid contacting devices in said lower adiabatic-stripping zone;
a liquid distributor receiving urea and carbamate solution from the upper reaction zone and distributing said solution over said gas-liquid contacting devices a bottom gas distributor providing the $CO_2$ feed in the adiabatic-stripping zone;
a chimney with a liquid seal, separating the upper reaction zone from the lower adiabatic-stripping zone, said liquid seal allowing to recycle a vapour phase containing ammonia and carbon dioxide from the lower stripping zone to the upper reaction zone of the reactor.

8. A method for revamping an urea plant comprising a high-pressure synthesis loop with at least a synthesis reactor receiving an ammonia feed and a carbon dioxide feed, a stripping section comprising at least one stripper, and a condensation section comprising at least one carbamate condenser, the method being characterized by:

providing at least a further adiabatic carbon dioxide stripping section in said synthesis loop;

providing appropriate means feeding the urea solution produced in said reactor to said adiabatic stripping section, and feeding a urea solution recovered from said adiabatic stripping section to the downstream thermal stripping section;

providing further means recycling a gaseous phase containing carbon dioxide and ammonia recovered in said adiabatic stripping section to the reaction zone in said synthesis reactor, and wherein said adiabatic stripping section is realized by modifying the synthesis reactor, providing an upper reaction zone and a lower adiabatic-stripping zone in said reactor, the adiabatic-stripping zone receiving the liquid urea solution coming from the upper reaction zone, the method further comprising the provision of means for feeding the upper reaction zone with a flow of ammonia plus recycled carbamate, and a carbon dioxide flow; and the provision of means for feeding a further $CO_2$ to said adiabatic-stripping zone.

9. A method according to claim 8, wherein the revamped plant is run with N/C ratio in the reactor between 4 and 6, while the N/C ratio of the urea solution at the inlet of the thermal stripper is between 2 and 4.

10. The process according to claim 2, wherein the synthesis reactor is run with N/C ratio around 4.5, while the N/C ratio of the urea solution at the inlet of the thermal stripping section is around 2.6.

* * * * *